United States Patent [19]

Nash

[11] Patent Number: 4,747,406

[45] Date of Patent: May 31, 1988

[54] SHAFT DRIVEN, FLEXIBLE INTRAVASCULAR RECANALIZATION CATHETER

[75] Inventor: John Nash, Downingtown, Pa.

[73] Assignee: Intravascular Surgical Instruments, Inc., Frazer, Pa.

[21] Appl. No.: 701,063

[22] Filed: Feb. 13, 1985

[51] Int. Cl.⁴ .............................. A61F 17/32
[52] U.S. Cl. ............................ 128/305; 604/22
[58] Field of Search .......... 128/305, 751, 305.1, 128/755, 310; 604/22, 595, 752

[56] References Cited

U.S. PATENT DOCUMENTS

| 1,481,078 | 1/1924 | Albertson . | |
| 1,636,036 | 7/1927 | Bolozky et al. . | |
| 2,570,335 | 10/1951 | Fitch | 64/2 |
| 2,761,297 | 9/1956 | Buchsteiner | 64/2 |
| 3,058,473 | 10/1962 | White head | 604/95 |
| 3,976,077 | 8/1976 | Kerfoot, Jr. | 128/305 |
| 4,177,797 | 12/1979 | Baylis et al. | 128/310 |
| 4,424,045 | 1/1984 | Kulischenko et al. | 464/52 |
| 4,445,509 | 5/1984 | Auth | 128/305 |
| 4,541,423 | 9/1985 | Barber | 128/305.1 |

Primary Examiner—C. Fred Rosenbaum
Assistant Examiner—H. Macey
Attorney, Agent, or Firm—Caesar, Rivise, Bernstein, Cohen & Pokotilow, Ltd.

[57] ABSTRACT

A recanalization catheter comprising a very small diameter elongated, flexible tubular member having a distal end at which a tool is mounted for high speed rotation. A flexible drive assembly is located within the tubular member and is connected to the tool. The drive assembly includes a flexible drive shaft mounted within plural spaced bearings to enable the shaft to be rotated at a very high rate of speed from a remotely located motor. The bearings serve to keep the drive shaft centered even as the catheter is bent through a sharp radius of curvature, while also preventing the shaft from going into critical whirl.

27 Claims, 3 Drawing Sheets

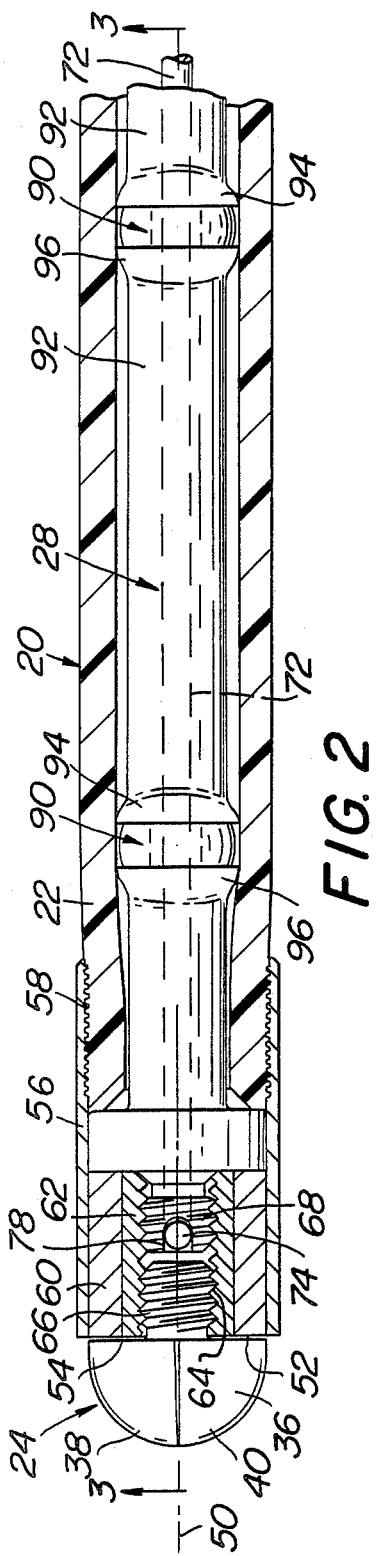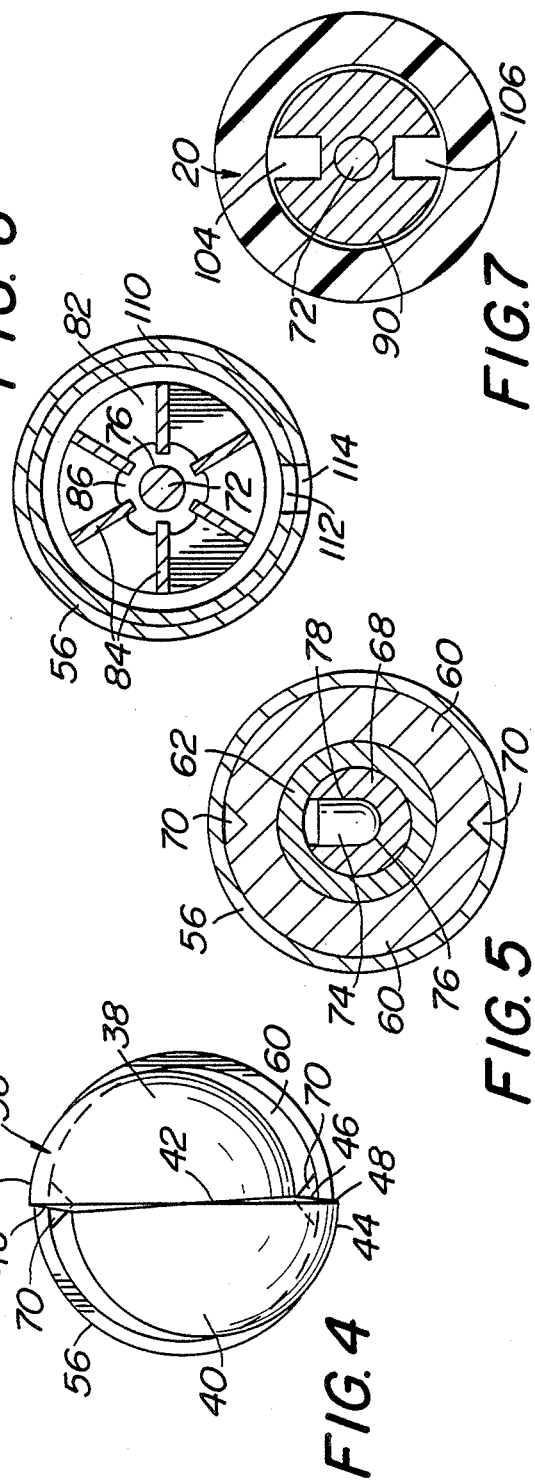

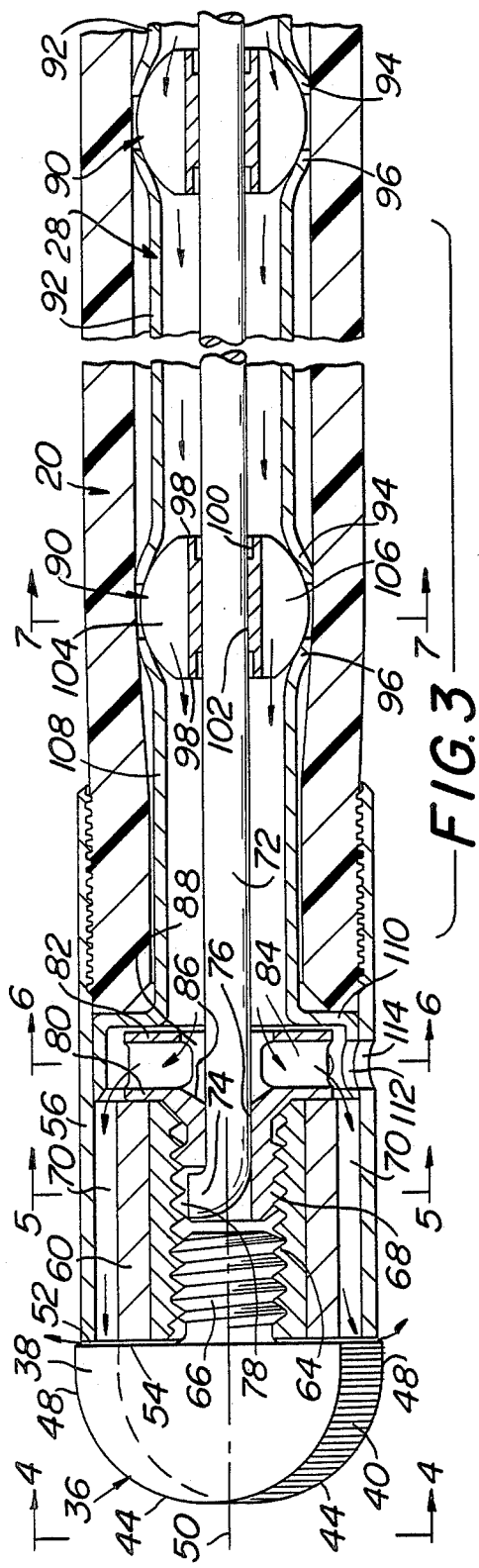
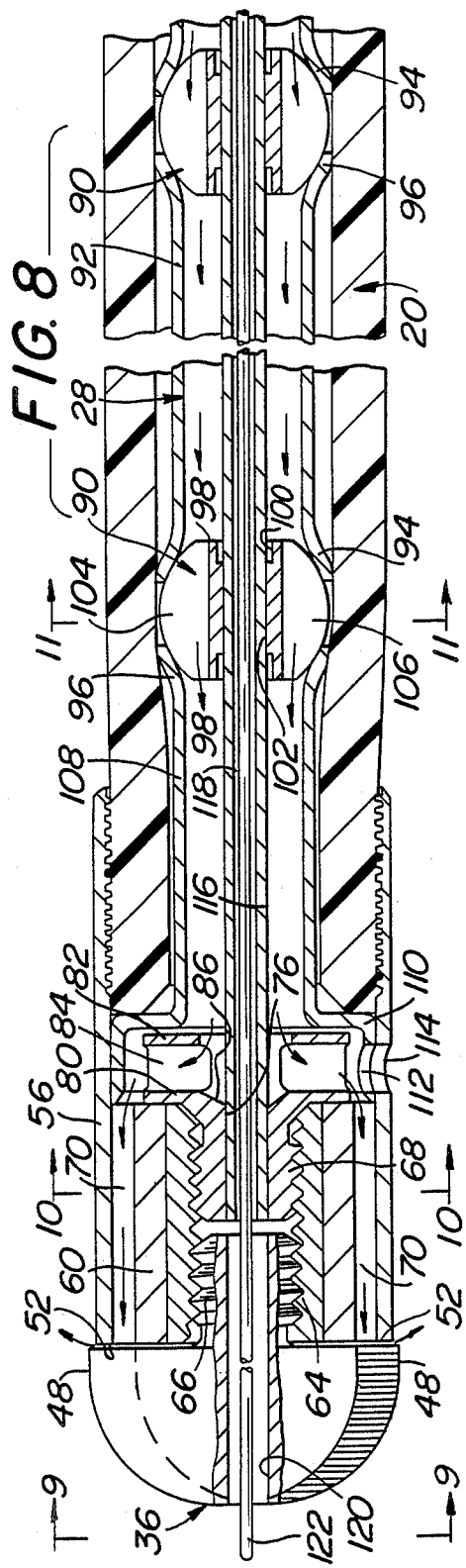

SHAFT DRIVEN, FLEXIBLE INTRAVASCULAR RECANALIZATION CATHETER

BACKGROUND OF THE INVENTION

This invention relates generally to flexible drive devices and more particularly to flexible drive, recanalizing catheters for intravascular surgery.

In U.S. Pat. No. 4,445,509 (Auth) there is disclosed a catheter apparatus for recanalizing (opening) a passageway, e.g., an artery, which has been occluded by intra-arterial deposits of atherosclerotic plaque. That recanalization catheter includes a multi-fluted, rotary cutting head mounted at the distal end of the catheter and arranged to be rotated by a flexible drive shaft extending down the center of the catheter. The drive shaft is arranged to be rotated within the catheter by an electric motor coupled to the proximal end thereof. The drive shaft is disclosed as being a steel helical coil of approximately 0.05 inch (1.3 mm) diameter. Such a coil is stated in the patent to be successful in transmitting high rotational speed (greater than 25,000 rpm) in a controlled fashion and with mechanical security.

Other prior art devices utilizing flexible drive shafts for conveying rotary power to a working head or tool are disclosed in the following U.S. Pat. Nos.: 1,481,078 (Albertson), 1,636,038 (Bolozsky et al.), 2,570,335 (Fitch), 2,761,297 (Buchsteiner et al.) and 4,424,045 (Kulischenko et al.).

In order for a recanalizing catheter to have wide applicability of use in intravascular surgery, its length should be sufficiently large, e.g., 2 to 3 feet or more, while its outside diameter, at least adjacent the working end, is sufficiently small, e.g., 3-4 mm. Moreover the catheter should be able to bend through a minimum diameter radius of curvature of 3 inches or less, in order to reach small, remotely located restrictions, e.g., occlusions.

As will be appreciated by those skilled in the art the torsional shear stress produced on a flexible drive shaft (e.g., a wire) will differ for different composition wires, e.g., approximately 150,000 psi for steel wires, 70,000 psi for beryllium-copper wires. If the radius of curvature through which the drive shaft must bend is very small, e.g., less than 3 inches, high bending stresses will be induced therein. In order to reduce bending strain the diameter of the flexible drive shaft or wire must be made very small, e.g., 0.02 or less inches. If the restriction opening tool is to be operated at a high rate of speed, e.g., greater than 20,000 rpm, in order to provide sufficient power at low torque, the deleterious dynamic effects of critical whirl and friction caused by high side loads on the bearing surfaces supporting the drive wire must be overcome or minimized while the positional neutrality (centering) of the drive shaft is maintained in order to insure that proper operation ensues. The flexible drive systems of the prior art as set forth above appear to leave much to be desired from the standpoint of effectiveness and efficiency of operation in applications involving high speed, small diameter, and small radius of curvature.

OBJECTS OF THE INVENTION

Accordingly, it is the general object of the instant invention to provide a flexible drive assembly which overcomes the disadvantages of the prior art.

It is a further object of the instant invention to provide a flexible drive assembly which is suitable for use in an intravascular recanalizing catheter.

It is a further object of the instant invention to provide a flexible drive assembly for use in a recanalizing catheter which is of very small diameter, can be bent through a small radius of curvature while operating at a high rate of speed, and without the drive assembly going into critical whirl.

It is a further object of this instant invention to provide a flexible drive assembly for use in a recanalizing catheter which is of very small diameter, can be bent through a small radius of curvature, yet which maintains positional neutrality with respect to said catheter at all times.

It is a further object of this instant invention to provide a flexible shaft driven recanalization catheter which is suitable for effecting the opening of a restriction in a passageway within a living being and without significant damage to said passageway.

SUMMARY OF THE INVENTION

These and other objects of the instant invention are achieved by providing apparatus for opening a restriction formed of material inside of a passageway within a living being. The apparatus comprises a flexible catheter having a distal end portion and a proximal end portion and being capable of being bent up to a predetermined minimum radius of curvature. A movable working head is located at the distal end portion of the catheter. The flexible drive means extends through the catheter and is coupled to the working head. The drive means comprises an elongated flexible drive shaft of small diameter and having a longitudinal central axis. The drive shaft extends from the proximal end portion of the catheter to the distal end portion. The flexible drive shaft is adapted to be rotated at a high rate of speed about its central axis. Bearing means comprising plural bearing surfaces are provided in the catheter for supporting portions of the drive shaft at predetermined longitudinally spaced positions therealong to maintain it at a neutral position therein as the catheter is bent through any arc up to the minimum radius of curvature while enabling the drive shaft to be rotated about the central axis at a high rotational speed without going into critical whirl.

DESCRIPTION OF THE DRAWING

Other objects and many of the attendant advantages of this invention will be readily appreciated as the same becomes better understood by reference to the folowing detailed description when considered in connnection with the accompanying drawing wherein:

FIG. 2 is an enlarged, side elevational view, partially in section, showing the distal end of the catheter device of FIG. 1;

FIG. 3 is an enlarged sectional view taken along line 3-3 of FIG. 2;

FIG. 4 is an end view of the catheter and taken along line 4—4 of FIG. 3;

FIG. 5 is a sectional view taken along line 5—5 of FIG. 3;

FIG. 6 is a sectional view taken along line 6—6 of FIG. 3;

FIG. 7 is a sectional view taken along line 7—7 of FIG. 3;

FIG. 8 is a sectional view, like that of FIG. 3, but showing an alternative embodiment of a recanalization catheter constructed in accordance with the subject invention;

DETAILED DESCRIPTION OF THE PREFERRED EMBODIMENT

Figure 1:
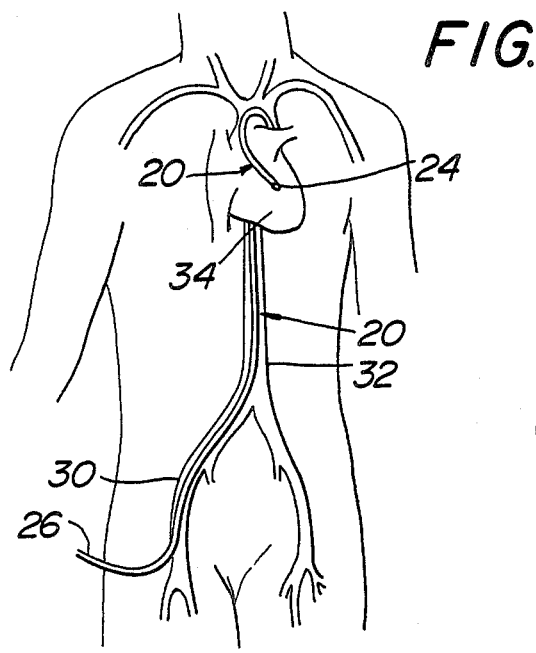
FIG. 1 is an illustration of a portion of the human vascular system showing one possible site for the introduction of a recanalization catheter device constructed using the teachings of this invention.
Figure 9:
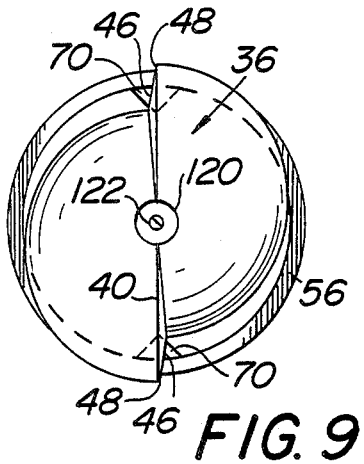
FIG. 9 is a view similar to that of FIG. 4 but taken along line 9—9 of FIG. 8.
Figure 10:
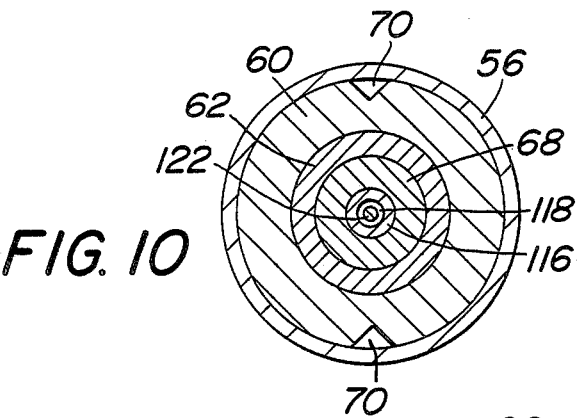
FIG. 10 is a sectional view taken along line 10—10 of FIG. 8.
Figure 12:
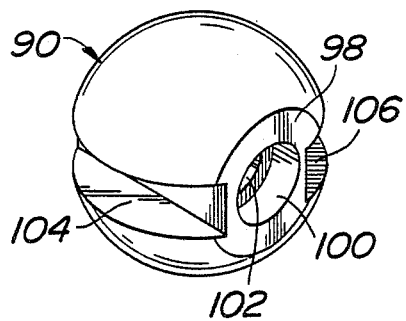
FIG. 12 is an enlarged perspective view of one bearing member of the drive assembly of the subject invention.
Figure 11:
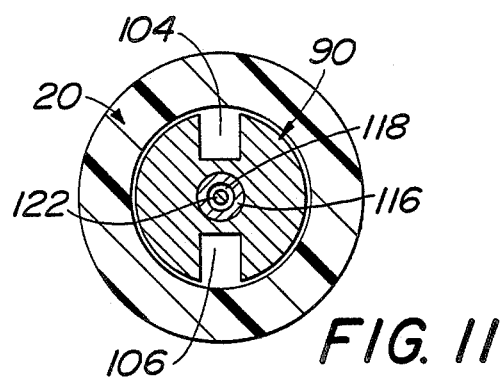
FIG. 11 is a sectional view taken along line 11—11 of FIG. 8.

Referring now in greater detail to the various figures of the drawing wherein like reference characters refer to like parts, there is shown at 20 in FIG. 1 recanalizing catheter 20 for intravascular or other surgical applications. The catheter 20 includes a flexible drive assembly constructed in accordance with the subject invention. The drive assembly will be described in considerable detail later and is particularly suited for intravascular surgical applications, but can be used for other applications requiring the transmission of power at high speed and low torque through a very narrow path including bends of small radius of curvature.

The recanalizing catheter 20 is shown in FIG. 1 in one operative position disposed within a portion of the vascular system of the human body. Such an application is only one of numerous surgical applications for the catheter. As can be seen in FIGS. 1 and 2 the catheter 20 is an elongated, flexible device having a distal end portion 22 at which a working head or tool 24 is mounted, and a proximal end portion 26, which is adapted to be connected to a source of rotary power, e.g., an electric motor (not shown). The catheter 20 includes the heretofore mentioned drive assembly, now designated by the reference numeral 28 (FIG. 2), and which extends the length of the catheter to drive, e.g., rotate, the working head 24 under the power provided from the remote power source.

In use, the catheter 20 is introduced into the vascular system such as through an opening in the femoral artery 30 at a point in the groin of the patient remote from the site of the vascular occlusion or blockage that has been determined to exist in an artery (e.g., a coronary artery). To that end the catheter is then passed via the aorta 32 into the heart 34 and then into the desired coronary artery to the point at which the working head 24 is located immediately adjacent the restriction, e.g., partial occlusion or full occlusion. As will be recognized by those skilled in the art such restrictions are formed by the deposit of atherosclerotic plaque or some other material(s), such as waxy and/or calcified atheroma, thickened and/or ulcerated intima, etc.

In the catheter embodiment shown herein the working head or tool 24 comprises a rotary cutter 36. The cutter is mounted at the distal end of the drive assembly 28 and constitutes one exemplary embodiment of my joint invention with another in a rotary cutter for use in intravascular surgery and which invention is the subject of a patent application to be filed later. Thus, the specific cutter 36 shown herein constitutes a dual-bladed embodiment of that joint invention.

As can be seen in FIGS. 2, 3 and 4 the cutter 36 basically comprises a solid bodied element whose outer distal periphery is in the form of a pair of convex sections 38 and 40 which are slightly laterally offset from each other along a divider line 42. The intersection of the convex surface 44 of each section with a planar surface 46 contiguous with the divider line 42 forms an arcuate cutting edge or blade 48.

In accordance with the teachings of my aforementioned joint invention, the cutter may be made up of any number of sections, thereby forming a device having any number of arcuate blades, with each blade preferably including at least one portion having a negative or zero degree rake. In the embodiment shown herein each blade is at a negative rake angle of approximately 10°.

The cutter 36 is arranged to be rotated at a high rate of speed, e.g., in excess of 20,000 rpm, about the longitudinal central axis 50 (FIG. 2) of the catheter under power provided from the remote power source, via the flexible drive assembly 28 of the catheter. In order to cool and lubricate the drive assembly a fluid is passed through the interior of the catheter from an entrance point adjacent the proximal end thereof. Moreover, the fluid is arranged to exit from the catheter at the distal end thereof through a narrow interface 52 between the distal end of the catheter 20 and the proximal face of the cutter 36. The exiting fluid has the advantageous effect of providing positive pressure to the wall of the artery contiguous with the cutter, thereby causing the artery wall to move slightly outward radially, that is away from the cutter, so that no damage to the artery wall by the cutter occurs. In addition the flow of fluid outward through the interface 52 also precludes fine fibrous tissue of the artery from gaining ingress into the interface where it could snag or spool-up. Moreover, the rotating cutter blades impart momentum to the exiting fluid, which action applies further positive pressure to the artery wall, thereby further decreasing the chances of tissue-snagging.

The restriction opening process is carried out by advancing the catheter as its cutter 36 rotates into the material making up the restriction so that the rotating cutter blades 48 engage that material. In some instances, e.g., hard or calcified deposits, an opening in the restriction is created by the rotating cutter blades actually cutting away or emmulsifying particles of the material(s) making up the restriction. In other instances, e.g, waxy or soft deposits, the material(s) of the restriction may merely be mechanically agitated, beaten or otherwise disturbed by the blades of the rotating cutter, whereupon an opening is created in the restriction by the movement of the material(s) without such material(s) actually being cut-up or removed from the restriction. In either case an opening permitting the freer flow of blood through the restriction results.

As can be seen in FIG. 3 the radial distance of the cutting edge 48 of each blade immediately adjacent the proximal face of the cutter, when measured from the longitudinal central axis 50, is slightly longer than the radial distance from that axis to the outside surface of the distal end portion of the catheter. This feature insures that a slight space is created between the inner surface of the artery wall and the entrance to the interface 52 between the cutter 36 and the end of the catheter, again in the interest of deterring any snagging or spooling action of the fiberous tissue of the artery wall within the interface.

The details of the catheter 20 will now be described. As can be seen the catheter 20 basically comprises an elongated, flexible tubular member of small outside diameter, e.g., 3 mm (10 French) or less. The inside diameter of the catheter is approximately 1.8 mm. At the distal end 22 of the catheter there is secured a sleeve 56 forming one portion of the mount for the cutter 36. The sleeve 56 is secured onto the distal end of the catheter via internal threads 58 on its proximal end which mate with corresponding threads on the distal end of the catheter. A sleeve bearing 60 is mounted within the sleeve 56 and serves to support for rotation about axis 50 a connector shaft 62. The connector shaft 62 is a cylindrical member located within the central bore of the sleeve bearing 60. The shaft 62 serves as a releasable mount for the cutter 36 while connecting the same to the distal end of the drive assembly 28. Thus connector shaft 62 itself includes a threaded central bore 64. The threaded bore is adapted to receive therein a correspondingly threaded extension 66 projecting from the proximal face 54 of the cutter 36 and centered on the central axis 50. The distal end of the drive assembly 28 includes drive shaft terminator 68. As can be seen clearly in FIGS. 2 and 3 the terminator 68 also includes an externally threaded, centrally located, extension portion which is threadedly engaged in the threaded bore 64 of the connector shaft 62.

As can be seen in FIG. 5 the sleeve bearing 60 includes a pair of V-shaped grooves 70 extending longitudinally down the length of the bearing along its outer periphery and located at diametrically opposed positions. The grooves 70 are enclosed by the contiguous inner surface of the sleeve 56 to form a pair of fluid passageways for carrying the fluid from the interior of the catheter 20 to the interface 52 for egress therefrom, as shown by the arrows in FIG. 3.

Referring now to FIGS. 2, 3, 7 and 12 the details of the drive assembly 28 will be described. Thus, the drive assembly 28 basically comprises an elongated flexible drive shaft, which in the embodiment shown in FIGS. 2-8, consist of a continuous length of a solid bodied wire 72. The wire is formed of a suitable high strength material, e.g, steel, and is of very small diameter, e.g, 0.02 inches (0.5 mm) or less, in the interest of flexibility. The wire 72 extends down the central axis of the catheter for the entire length thereof, that is from the power source (not shown) at the proximal end of the catheter to the terminator 68 at the distal end. In particular the distal end 74 of the wire 72 extends through a central opening 76 in the wire terminator. The free end 74 of the wire is bent perpendicular to the longitudinal axis 50 and is located within a locking slot 78 in the terminator. This action secures the wire terminator 68 to the wire 72 so that rotation of the former about longitudinally axis 50 causes the latter to rotate concomitantly therewith.

As can be seen in FIGS. 3 and 6 the proximal end of the wire terminator 68 is in the form of a rotor-like portion having a front wall 80, a rear wall 82, and a plurality of radially extending intermediate blades 84 projecting outward from a central hub 86 (FIG. 6). The central opening 76 in the terminator extends through the hub 86 and includes an enlarged bore portion 88 (FIG. 3) at the proximal end thereof and which is in fluid communication with the spaces between the blades 84.

Fluid to cool and lubricate the drive assembly is arranged to flow through the hollow interior of the catheter 20 past the drive assembly 28 and into the wire terminator's bore 88 from which it flows radially outward and into the proximal ends of the two V-shaped passageways 70, as shown by the arrows in FIG. 3.

In order to maintain the wire 72 in a neutral, that is centered, position within the catheter 20 even when the catheter is bent through the very small (minimum) radius of curvature to be expected in intravascular surgical applications, while also precluding the wire from going into critical whirl as it is rotated at its high operating speed, the drive assembly 28 also includes plural bearings 90. Thus, the bearings support the wire centered within the catheter to enable it to rotate at the high speed without damage. The bearings are spaced from one another longitudinally by plural spacer elements 92 so that the centers of the bearings, that is the portions supporting the wire 72, are no further apart than one-half of the wave length of the stationary or standing wave which would naturally result from the rotation of an unsupported wire at that rotational speed. In a preferred embodiment of the invention for wires of no larger than approximately 0.02 inch (0.5 mm) and which are to be rotated at speeds in excess of 20,000 rpm, the spacing (pitch) of the bearings should be no larger than 0.5 inch (0.64 cm) and preferably 0.375 inch (0.95 cm).

As can be seen clearly in FIGS. 2 and 3, each spacer 92 is an elongated tubular member having a pair of flared ends 94 and 96. Each bearing 90 is located between the trailing flared end 96 of one spacer and the leading flared end 94 of the next succeeding, proximally located, spacer. A typical bearing 90 is shown in perspective in FIG. 12, in elevation in FIG. 2, and in section in FIG. 3. As can be seen therein, each bearing is of a generally ball-like shape. As will be appreciated, the construction and the location of immediately adjacent flared ends of immediately adjacent spacers form what can be referred to as a raceway or seat for the bearing. By virtue of the fact that the free edges of the adjacent flared ends of the spacers are slightly separated from each other, the spacers can pivot with respect to each other about the bearing when the catheter is bent, that is, the central longitudinal axis of each of any two immediately adjacent spacers will extend at an angle to the other instead of being colinear as is shown in FIG. 3. The greatest deviation from colinearity that adjacent spacers can assume with respect to each other is a function of the geometry of the bearings and spacers, and, in the preferred embodiment disclosed herein, occurs when the catheter is bent through the minimum radius of curvature of 3 inches (7.5 cm). At this point, edge portions of contiguous spacers abut to preclude further bending of the catheter.

Each of the bearings includes a pair of flat poles 98 connected by a central opening 100. The poles are located diametrically opposed to each other and perpendicularly to the central axis 50. The end of the central opening 100 contiguous with each of the poles is slightly greater in diameter than the mid-portion of the opening to create a central cylindrical bearing surface 102. The diameter of the bearing surface 102 is just slightly larger than the outside diameter of the wire 72 to support the wire centrally therein. Moreover each surface 102 forms a flex point for the wire to enable the catheter to be bent while maintaining the wire centrally located therein. Thus, when the catheter is bent through some arc the tubular spacers pivot with respect to each other while the wire 72 bends about the pivot surface 102 in each bearing but is generally straight and centered with respect to the spacer through which it passes between the bearings. Each bearing flex surface 102 is selected to be sufficiently short in length so that when the catheter is bent through its "minimum" radius of curvature, the portions of the bearing contiguous with the ends of the opening 100 do not interfere with the wire, while being long enough to provide a sufficient surface area to accept the anticipated sideloads at the sliding velocities to be encountered in operation so that damage to the bearings does not ensue. In the preferred embodiment constructed as specified above, the length of the bearing surface 102 for bearings constructed of conventional materials is no smaller than 0.02 inches (1 mm).

As mentioned earlier, fluid is provided through the interior of the catheter in order to cool and lubricate the wire drive components. In order to facilitate the passage of fluid down the catheter, each bearing 90 also includes at least two slots 104 and 106 therein. As can be seen clearly in FIGS. 7 and 12, the slots 104 and 106 are located in the periphery of the bearing at diametrically opposed locations and are disposed parallel to the central opening 100. Accordingly, fluid can be introduced into the most proximally located spacer 92 by means (not shown) from whence the fluid flows through the spacer, through the slots 104 and 106 in the bearing 90 and from there into the next spacer. This action continues so that the fluid flows down the entire length of the catheter to cool and lubricate the drive assembly.

As can be seen in FIG. 3, the most distally located bearing is interposed between a spacer 92 and an element 108 which acts like a spacer but which also serves as a bearing locator. The bearing locator element 108 thus includes a tubular portion constructed similarly to the spacers 92 and having a flared proximal end 96. The forward end of the element 108 includes an annular flanged portion 110 which is fixedly secured within the interior of the sleeve 56. The hollow interior of portion 110 is adapted to receive and hold the proximal end of the wire terminator 68 therein. In addition, the portion 110 serves to direct the fluid exiting out through the spaces between the ribs of the rotor portion of the terminator into the V-shaped passageways 70 as shown in FIG. 3.

The flanged portion 110 of locator element 108 also includes an opening 112 in its sidewall and which opening is aligned with a similar opening 114 in the sleeve 56. The aligned openings 112 and 114 form a spragging port for the rotor portion of the wire terminator 68 so that it can be locked against rotation via the insertion of a tool (not shown) within the ports. When the terminator is locked in position, the cutter 36 can be replaced by unscrewing it from within shaft 62. A different cutter (not shown) can then be screwed into place and the tool removed from the spragging port to ready the catheter for operation.

In FIG. 8 there is shown an alternative embodiment of a recanalizing catheter constructed in accordance with the subject invention. The embodiment shown in FIG. 8 is identical in most respects to the embodiment disclosed heretofore. The major differences in the embodiment in FIG. 8 are that the drive assembly does not use a solid bodied drive shaft (wire) but rather uses a tubular or hollow wire drive shaft and the cutter includes a central opening in it. The opening in the cutter is aligned with the central passageway in the tubular drive shaft to enable a conventional guidewire to be passed therethrough to facilitate the placement of the recanalizing catheter at the desired arterial site.

Inasmuch as most of the features of the catheter shown in FIG. 8 are the same as that described heretofore, the same reference numerals will be used herein for those identical parts and such parts will not be described in detail again in the description of FIG. 8 to follow.

As can be seen in FIG. 8, the wire drive assembly 28 of the alternative catheter includes the heretofore described bearings 90 and spacers 92. The bearings support a longitudinally extending, centrally located, flexible drive shaft 116. The drive shaft is in the form of a tubular wire formed of a suitable material, e.g., steel, and provides the same function as the heretofore described solid bodied wire 72. The interior of the drive shaft 116 is in the form of a central passageway 118 extending the full length thereof. The distal end of the tubular drive shaft 116 is fixedly secured within a central opening in the wire terminator 68. As mentioned earlier the cutter 36 includes a central opening 120 therein extending through the cutter itself and its threaded mount 66. The opening 120 is aligned with the passageway 118 in the tubular drive shaft. The inside diameter of the passageway 118 and the opening 120 are each sufficiently large to freely accommodate the outside diameter of the conventional guidewire 122 extending therethrough.

The catheter of FIG. 8 is arranged to be guided to its operative position within the artery by the use of the guidewire 122. This action is accomplished by inserting the guidewire at the appropriate selected site in the body, such as into the femoral artery. The guidewire is then passed via the aorta 32 into the coronary artery to the location of the restriction. The introduction of the guidewire can be aided by a fluoroscope, and a contrast medium can also be introduced into the artery. The recanalizing catheter of FIG. 8 is then threaded down the guidewire 122, via the opening 120 in the cutter 36 and the passageway 118 in the drive shaft to the position at which the cutter is located immediately adjacent the proximal end of the restriction to be opened. Fluid is then introduced into the catheter from a point adjacent the proximal end of the catheter. The fluid flows down the catheter in the direction of the arrows shown to cool the drive assembly while exiting through the interface 52 between the cutter and the distal end of the catheter. As described earlier this exiting fluid flow applies positive pressure to the artery wall to move the artery wall outward slightly radially so that damage to the wall by the cutter does not occur. In addition, the flow of fluid outward through the interface also precludes any fibrous tissue from snagging.

The fluid which is passed down the cathter can, if desired, be oxygenated to eliminate distal ischemia during the restriction opening procedure. Also, if desired, nitrates, contrast medium or other drugs can be added to the fluid as needed during the procedure.

Without further elaboration, the foregoing will so fully illustrate my invention that others may, by applying current or future knowledge, readily adopt the same for use under various conditions of service.

I claim:

1. Apparatus for opening a restriction formed of material inside of a passageway within a living being, said apparatus comprising: a flexible catheter having a distal end portion and a proximal end portion and being capable of being bent through a predetermined minimum radius of curvature, movable working means located at said distal end portion, and drive means coupled to said working means for moving said working means, said drive means comprising an elongated flexible drive shaft of small diameter having a longitudinal central axis and extending from said proximal end to said distal end portion, said drive shaft being adapted to be rotated at a high rate of speed about said central axis, a plurality of bearing means comprising plural bearing surfaces supporting portions of said drive shaft at predetermined longitudinally spaced locations therealong to maintain said drive shaft at a neutral position within said catheter as said catheter is bent through any arc up to said minimum radius of curvature, while enabling said drive shaft to be rotated about said central axis at said high rotational speed without resulting in excessive vibration which could interfere with the restriction opening procedure and spacer means free of said drive shaft and disposed between said bearing means for maintaining said predetermined spacings between said bearing means.

2. The apparatus of claim 1 wherein said bearing means comprises plural bearings, each of said bearings having an opening therein forming said bearing surface and through which said drive shaft extends, said bearings being arranged to pivot with respect to said catheter as said catheter is bent so that said drive shaft is maintained in said neutral position.

3. The apparatus of claim 2 wherein said spacer means is spaced from said drive shaft and disposed between said bearings for maintaining said predetermined spacings between said bearings.

4. The apparatus of claim 2 wherein said bearings are ball-like.

5. The apparatus of claim 4 wherein said tubular spacing means surrounds and is spaced from said drive shaft and is disposed between said bearings to maintain said predetermined spacing.

6. The apparatus of claim 5 wherein each of said tubular spacers includes a pair of enlarged diameter free ends and wherein each of said bearings is disposed between the free end of one tubular spacer and the free end of the next succeeding tubular spacer.

7. The apparatus of claim 2 wherein the opening in each of said bearings is of a first predetermined length sufficiently short to provide adequate clearance for said drive shaft when said catheter is bent to said minimum radius of curvature.

8. The apparatus of claim 1 wherein said working means is a rotary member.

9. The apparatus of claim 8 wherein said bearing means comprises plural bearings, each of said bearings having an opening therein forming said bearing surface and through which said drive shaft extends, said bearings being arranged to pivot with respect to said catheter as said catheter is bent so that said drive shaft is maintained in said neutral position.

10. The apparatus of claim 9 wherein the opening in each of said bearings is of a first predetermined length sufficiently short to provide adequate clearance for said drive shaft when said catheter is bent to said minimum radius of curvature.

11. The apparatus of claim 10 wherein said drive shaft comprises a wire including a distal end to which said working means is connected.

12. The apparatus of claim 11 wherein said wire is tubular and wherein said working means includes an opening therein, whereupon a guidewire can be inserted through the length of said catheter to facilitate the placement of said catheter within said passageway.

13. The apparatus of claim 1 wherein said catheter is hollow and adapted to receive a fluid flow therethrough between said catheter and said drive shaft from a point adjacent the proximal end to the distal end.

14. The apparatus of claim 13 wherein said bearing means comprises plural bearings, each of said bearings having an opening therein forming said bearing surface and through which said drive shaft extends, said bearings being arranged to pivot with a respect to said catheter as said catheter is bent so that said drive shaft is maintained in said neutral position.

15. The apparatus of claim 14 wherein said fluid flows through said bearings.

16. The apparatus of claim 13 wherein said working means is a rotary member and said working means is spaced from the distal end of said catheter, whereby passing a fluid through said catheter causes said fluid to flow out through the interface between said working means and the distal end of said catheter.

17. The apparatus of claim 16 further comprising: a fixed bearing at the distal end of said catheter; and connector means within said fixed bearing, said connector means being connected to the distal end of said drive shaft and to said working means.

18. The apparatus of claim 17 wherein said working means is releasably secured to said connector means.

19. A flexible drive assembly comprising an elongated tubular member of unitary construction having a rear portion and a front portion, an elongated flexible member of small diameter having a longitudinal central axis extending within said tubular member from said rear end portion to said front end portion thereof, said flexible member being adapted to be rotated at a high rated speed about its central axis by a source of power coupled to its rear end portion, bearing means within said tubular member comprising plural bearing surfaces for supporting portions of said elongated flexible member at predetermined longitudinal spaced locations therealong and for maintaining said flexible member at a neutral position within said tubular member as said tubular member is bent through any angle up to a predetermined small radius of curvature, while enabling said member to be rotated about said central axis at said high rotational speed without said member going into excessive vibration, said bearing means being comprised of plural bearings, each of said bearings having an opening therein forming said bearing surface and through which said elongated flexible member extends, said bearing means being arranged to pivot with respect to said tubular member as said tubular member is bent so that said flexible member is maintained in said neutral position.

20. The apparatus of claim 19 wherein said assembly additionally comprises spacer means spaced from said flexible member and extending between said bearings for maintaining said predetermined spacings between said bearings.

21. The apparatus of claim 19 wherein the opening in each of said bearings is of a first predetermined length sufficiently short to provide adequate clearance for said flexible member when said tubular member is bent to said predetermined radius of curvature.

22. The flexible drive assembly of claim 19 wherein a fluid is provided into the interior of said tubular member to cool and lubricate said bearing means.

23. The flexible drive assembly of claim 22 wherein each of said bearings includes at least one fluid passageway therein.

24. The flexible drive assembly of claim 23 additionally comprising spacer means spaced from said flexible member and disposed between said bearings for maintaining said predetermined spacings between said bearings.

25. The flexible drive assembly of claim 24 wherein each of said spacers comprises an elongated tube spaced from said flexible member and through which said fluid is arranged to flow.

26. The flexible drive assembly of claim 19 additionally comprising coupling means at said front end thereof and connected to the front end of said flexible member, said coupling means being arranged to releasably secure a tool thereon.

27. The flexible drive assembly of claim 26 additionally comprising other bearing means supporting said coupling at the front end of said drive assembly.

* * * * *